United States Patent [19]

Miller

[11] Patent Number: 5,766,945
[45] Date of Patent: Jun. 16, 1998

[54] 10A1 RETROVIRAL PACKAGING CELLS AND USES THEREOF

[75] Inventor: A. Dusty Miller, Seattle, Wash.

[73] Assignee: Fred Hutchinson Cancer Research Center, Seattle, Wash.

[21] Appl. No.: 798,000

[22] Filed: Feb. 12, 1997

Related U.S. Application Data

[60] Provisional application No. 60/011,564, Feb. 13, 1996.

[51] Int. Cl.$^6$ .................. C12N 5/10; C12N 15/00; C12N 15/63
[52] U.S. Cl. .................. 435/325; 435/172.3; 435/320.1
[58] Field of Search .................. 435/325, 320.1, 435/172.3

[56] References Cited

U.S. PATENT DOCUMENTS

| | | | |
|---|---|---|---|
| 5,278,056 | 1/1994 | Bank et al. | 435/172.3 |
| 5,449,614 | 9/1995 | Danos et al. | 435/172.3 |
| 5,470,726 | 11/1995 | Miller et al. | 435/172.3 |

FOREIGN PATENT DOCUMENTS

| | | |
|---|---|---|
| 89/03882 | 5/1989 | WIPO. |
| 94/29438 | 12/1994 | WIPO. |
| 96/30504 | 10/1996 | WIPO. |
| 96/37623 | 11/1996 | WIPO. |

OTHER PUBLICATIONS

Fischinger et al., "A novel murine oncornavirus with dual eco–and xenotropic properties", *Proc. Natl. Acad. Sci.*, 72:5150–5155 (Dec., 1975).

Hartley et al., "a new class of murine leukemia virus associated with development of spontaneous lymphomas", *Microbiology*, 74:789–792 (Feb., 1977).

Chatopadhyay et al., "Origin of Mink Cytopathic Focus-Forming (MCF) Viruses: Comparison with Ecotropic and Xenotropic Murine Leukemia Virus Genomes", *Virology*, 133:465–483 (1981).

Rasheed et al., "Characterization of a Highly Oncogenic Murine Leukemia Virus from Wild Mice", *Int. J. Cancer*, 29:345–350 (1982).

Rein et al., "Different Recombinant Murine Leukemia Viruses Use Different Cell Surface Receptors", *Virology*, pp. 144–152 (1984).

Ott et al., "Sequence Analysis of Amphotropic and 10A1 Murine Leukemia Viruses: Close Relationship to Mink Cell Focus–Inducing Viruses", *Journal of Virology*, pp. 757–766 (Feb., 1990).

Miller, "Retrovirus Packaging Cells", *Human Gene Therapy*, 1:5–14 (1990).

Miller et al., "Construction and Properties of Retrovirus Packaging Cells Based on Gibbon Ape Leukemia Virus", *Journal of Virology*, pp. 2220–2224 (May, 1991).

Ott et al., "Basis for Receptor Specificity of Nonecotropic Murine Leukemia Virus Surface Glycoprotein gp70$^{SU}$", *Journal of Virology*, pp. 4632–4638 (Aug., 1992).

Miller et al., "Cloning of the cellular receptor for amphotropic murine retroviruses reveals homology to that for gibbon ape leukemia virus", *Proc. Natl. Acad. Sci.*, 91:78–82 (Jan., 1994).

van Zeijl et al., "A human amphotropic retrovirus receptor is a second member of the gibbon ape leukemia virus receptor family", *Proc. Natl. Acad. Sci.*, 91:1168–1172 (Feb., 1994).

Miller et al., "Hybrid Proteins That Functions As Receptors For Both Amphotropic Murine Retroviruses And GALV", *Abstracts of papers presented at the 1994 meeting on Retroviruses*, p.37 (May, 1994).

Miller et al., "A Family of Retroviruses That Utilize Related Phosphate Transporters for Cell Entry", *Journal of Virology*, pp. 8270–8276 (Dec., 1994).

Markowitz, et al., "A Safe Packaging Line for Gene Transfer: Separating Viral Genes on Two Different Plasmids," *J. Virol.*, 62:1120–1124 (Apr., 1988).

Miller et al., "Retrovirus Packaging Cells based on 10A1 Murine Leukemia Virus for Production of Vectors that use Multiple Receptors for Cell Entry," *J. Virol.* 70:5564–5571 (Aug., 1996).

Naviaux, et al., "The PCL Vector System: Rapid Production of Helper–Free, High–Titer, Recombinant Retroviruses," *J. Virol.* 70:5701–5705 (Aug., 1996).

Miller, "Cell–Surface Receptors for Retroviruses and Implications for Gene Transfer," *Proc. Natl. Acad. Sci. USA*, 93:11407–11413 (Oct., 1996).

*Primary Examiner*—Jasemine C. Chambers
*Assistant Examiner*—Deborah J. R. Clark
*Attorney, Agent, or Firm*—Townsend and Townsend and Crew LLP

[57] ABSTRACT

Retroviral packaging cells produce replication-defective retroviral vector particles capable of binding to Glvr-1 or Ram-1 retroviral receptors on target cells and are useful in gene therapy. The packaging cell employs a vector encoding a 10A1 retroviral env protein and produces the retroviral particles at high titer.

12 Claims, 4 Drawing Sheets

FIG. 2A

```
            Sph I
4070A  GCATGCCCGCCAGGTATTGGGAACTGACAATGGGCCCTGCCTTCGTCTCTCCAAGGTGAGTCAGA
10A1   -------T-------G----------------------------------------------
MoMLV  -------T------------------------------------------------------   60

4070A  CAGTGGCCCGATCTCTGTTGGGGATTGATTGGAAATTACATTGTGCATACAGACCCCAAAGCT
10A1   -----------------C---------------------------G-C--------------
MoMLV  --------------------------------------------------------------  120

4070A  CAGGTCAGGTAGAAAGAATGAATAGGACCATCAAGGAGACTTTAACTAAATTAACGCTTG
10A1   ------C-----------------------A------------------------------
MoMLV  --------------------A-----------------------------------------  180

4070A  CAACTGGCTCTAGAGACTGGGTGCTCCTACTCCCCTTAGCCCTGTACCGAGCCCGCAACA
10A1   --------A------------------A--------T---------C---------------
MoMLV  --------------------------------------------------------------  240

4070A  CGCCGGGCCCCATGCCCTCACCCCATATGAGATCTTATATGGGCACCCCCGCCCCCTTG
10A1   -T-------------A-------T---T--G----A--C-G----------G----------
MoMLV  --------------------------------------------------------------  300

4070A  TAAACTTCCCTGACCCTTAGTCCAGACATGACCAGAGTTACTAACAGCCCCTCTCTCCAAGCTCACT
10A1   -T--T----A---T----C-AGC---A--A-GA--G---C---AG----T---T--------
MoMLV  -------------A--------------T-A--AGT------A---------------------  360

4070A  TACAGGCTCTCTACTTAGTCCAGCACGAAGTTTGGAGACCACTGGCGGCAGCTTACCAAG
10A1   ------C--------C--AGC---A--A-GA---C---AG-----C--T--C--T--G-
MoMLV  --------------------------------C--------T-------C-----------  420

4070A  AACAACTGGACCGGGCCCGGTGCCCTCACCCCTTACCGGGTCGGGCGACAGTGTGGGTCC
10A1   -C--G------A-----A----A-A------A-------C-T--T---------C----A-
MoMLV  -------------A--------A-A----A--------------------------------  480
```

```
4070A TTTGACTTTTACCGTGTGCCCTGGGCATACCGTGTAAAGTCGGGGTGTGGGGACCA G G A G A  —1020
10A1  ------------------------------------A-----------------  A      —
                                                              ─────
4070A GGGCTACTGTGTGGT A A A T GGGGTGTGAAACCACCCGGACAGGCTTACTGGAAGCCCACATC —1080
10A1  ---------------  G       ---------------T------------------------
                     ─────
4070A ATCGTGGGACCTAATCTCCCTTAAGCCGGTAACACCCCTGGGACACGGGATGCTCTAA    —1140
10A1  ----A---------------------------------------------------C--

4070A AGTT GCCTGTGTGGCCCCTGCTACGACCTCTCTCCAAAGTATCCAATTCCTTCCAAGGGGCTAC —1200
10A1   A-G  T---------------------------------G------------------------
      ────                                   ⓖ
                                               Ⓣ
4070A TCGAGGGGGCAGATGCAACCCCTCTAGTCCTAGAATTC
10A1  --------------------------------------
      Xhol                                  EcoRI
```

| FIG. 2A |
|---|
| FIG. 2B |
| FIG. 2C |

FIG. 2

10A1 RETROVIRAL PACKAGING CELLS AND USES THEREOF

GOVERNMENT SUPPORT

This work was supported by grants DK47754 and HL36444 from the National Institutes of Health. The U.S. Government may have certain rights in the invention.

CROSS-REFERENCE TO RELATED APPLICATION

This application claims the benefit of U.S. Provisional Application No. 60/011,564, filed Feb. 13, 1996, the disclosure of which is incorporated by reference.

BACKGROUND OF THE INVENTION

Retroviral vectors promote the transfer of genes into a variety of cell types from many animal species. Retroviral vectors are among the primary vehicles used for gene transfer into human somatic cells because of their ability to transfer genes efficiently into cells that are difficult to transfect by other methods.

A critical element in the production of the components to carry out retroviral mediated gene transfer is the cell that generates the retroviral particles carrying the gene to be transferred. These cells are called "packaging cells" because they "package" the retroviral vector which carries the gene of interest into a delivery vehicle, the retroviral particles. Packaging cell lines are designed to synthesize all retroviral proteins required for assembly of high-titer infectious virus, but should not produce any replication-competent virus. Thus, the retroviral vector consists of DNA sequences intended for transfer flanked by signals present at the ends of the retroviral genome, and the packaging cells are designed to produce all of the retroviral proteins and promote "packaging" of the retroviral RNA into virions. Retroviral vectors produced by using packaging cells can thus infect cells but cannot replicate further.

Retrovirus packaging cells provide useful tools for a variety of gene transfer applications. However, not all cell types can be efficiently infected by using the available packaging cell lines. The range of cells that are infectable by a retroviral particle is primarily determined by the envelope proteins of the virus and the presence of appropriate receptors for this protein on the surface of target cells. For example, viruses that infect human cells can be separated into eight groups based on the use of different receptors for cell entry.

Recent improvements include the design of packaging cells to produce vectors having a vesicular stomatitis virus G protein coat for expanded host range (Burns et al., *Proc. Natl. Acad. Sci. USA* 90:8033-8037 (1993); Lin et al., *Science* 265:666-669 (1994)), vectors that are resistant to human serum (Cosset et al., (1995)), and vectors that target to new cell-surface proteins (Kasahara et al., *Science* 1373-1376 (1994); Somia et al., *Proc. Natl. Acad. Sci. USA* 92:7570-7574 (1995)). However, there is still room for improvement to increase the efficiency and range of cell types that can be transduced using existing retroviral vectors. For example, treatment of genetic and acquired disease in humans would be greatly facilitated by the ability to transfer genes into hematopoietic stem cells, but transduction of these cells in large animals and humans remains poor.

Packaging cells which produce amphotropic retrovirus (retroviruses which can infect cells from many species) were developed over ten years ago and are still commonly used because of the wide range of cell types from different species, including humans, that these vectors can transduce. (Cone et al., *Proc. Natl. Acad. Sci. USA* 81:6349-6353 (1984); Miller et al., *Mol. Cell. Biol.* 6:2895-2902 (1986); Miller et al., *Mol. Cell. Biol.* 5:431-437 (1985); and Sorge et al., *Mol. Cell. Biol.* 4:1730-1737 (1984)). More recently, packaging cells have been developed based on gibbon ape leukemia virus (GALV) (Miller et al., *J. Virol.* 65:2220-2224 (1991)) that produce vectors that use a different receptor for cell entry, and are capable of transducing myeloid, lymphoid, and airway epithelial cells at higher rates than amphotropic vectors do (Bauer et al., *Blood* 86:2379-2387 (1995); Bayle et al., *Hum. Gene Ther.* 4:161-170; Bunnell et al., *Proc. Natl. Acad. Sci. USA* 92:7739-7743 (1995); von Kalle et al., *Blood* 84:2890-2897).

The GALV and amphotropic retrovirus receptors are related phosphate transport proteins that exhibit wide, but different, patterns of tissue specific expression (Kavanaugh et al., *Proc. Natl. Acad. Sci. USA* 91:7071-7075 (1994)). The GALV receptor Glvr-1 (Pit-1) is most highly expressed in bone marrow, while the amphotropic receptor Ram-1 (Pit-2) is most highly expressed in the heart. It has been shown that 10A1 murine leukemia virus can use either mouse or human Glvr-1 or rat or human Ram-l for cell entry (Miller et al., *J. Virol.* 68:8270-8276 (1994)).

What is needed in the art is a retroviral packaging system that offers advantages over currently available viral packaging systems and that is useful in a wide variety of gene transfer applications. Quite surprisingly, the present invention fulfills this and other related needs.

SUMMARY OF THE INVENTION

In one aspect the invention provides a cultured packaging cell for producing a replication-defective retroviral vector particle. The packaging cell is a vertebrate cell capable of expressing and assembling retroviral proteins, and comprises a vector encoding a retroviral env protein having amino acid residues of 10A1 that direct binding of the retroviral particle to Glvr-1 or Ram-1 retroviral receptors on a target cell. The packaging cell further comprises a vector encoding oncoviral gag and pol genes, such that upon expression of the vectors in the presence of a vector having a sequence capable of encoding a heterologous gene of interest, a replication-defective retroviral vector particle is produced that binds to Glvr-1 and Ram-1 retroviral receptors of target cells. The vector encoding the retroviral env protein can encode the 10A1 env amino acid residues encoded within the BsrGI-XhoI fragment of the 10A1 env gene, such as a vector including the nucleotide sequence of the BsrGI-XhoI fragment of the 10A1 env gene. In another aspect the retroviral env protein can be a chimeric protein having non-10A1 env amino acid residues from a different amphotropic retrovirus. The oncoviral gag and pol genes can be from a retrovirus, such as an amphotropic retrovirus. The cultured packaging cell can be an avian or mammalian cell capable of expressing and assembling retroviral proteins. The vectors encoding the retroviral env protein, the oncoviral gag and pol proteins, and the sequence capable of encoding a heterologous gene of interest can be integrated in a chromosome of the packaging cell.

In another aspect the invention provides a method for producing a replication-defective retroviral vector particle encoding a heterologous gene of interest. The method comprises transducing or transfecting a retroviral packaging cell with (a) a replication defective virus particle which comprises virus RNA transcribed from a recombinant DNA provirus, the provirus comprising virus long terminal repeat sequences (LTRs), a retrovirus packaging sequence, and a heterologous gene, or (b) a vector comprising the provirus. The packaging cell can be a vertebrate cell capable of expressing and assembling retroviral proteins and having (i) an integrated vector encoding a retroviral env protein having amino acid residues of 10A1 that direct binding of the retroviral particle to Glvr-1 or Ram-1 retroviral receptors on a target cell, and (ii) an integrated vector encoding oncoviral gag and pol genes. The sequences which encode the retroviral env protein, the oncoviral gag and pol genes, and the sequence that encodes the heterologous gene of interest are expressed, producing a replication-defective retroviral vector particle that binds to Glvr-1 and Ram-1 retroviral receptors of target cells. The replication-defective retroviral vector particle, containing the heterologous gene of interest, can be produced at a titer of at least $10^5$ FFU/ml medium, and up to at least about $10^7$ FFU/ml medium. In another aspect the invention provides a replication-defective retroviral vector particle containing the heterologous gene of interest produced by this method.

BRIEF DESCRIPTION OF THE DRAWINGS

FIG. 2 shows the sequence of 10A1 and 4070A pol-env regions. 10A1 virus was sequenced from a SphI site in the pol gene to the EcoRI site in the env gene. 4070A amphotropic virus was sequenced from an SphI site in the pol gene to the PflMI site 12 bases upstream of the env start codon. The rest of the 4070A (Ott et al., *J. Virol.* 64:757–765 (1990)) and the MoMLV sequences (Shinnick et al., *Nature* 293:543–548 (1981)) depicted were obtained from GenBank and checked against the original publications. The sequence of 4070A is shown, and for the other sequences, dashes indicate bases that are identical to those in 4070A while letters indicate base differences. Blank spaces in the 4070A and MoMLV indicate the position of a 3 base insertion in 10A1 virus. MoMLV bases after base 737 are not shown because the following sequence was very divergent from those of 4070A and 10A1 and could not be meaningfully aligned. Circled bases indicate sequence differences between the present data (shown) and previous sequence analyses of 4070A and 10A1 (Ott et al., *J. Virol.* 64:757–765 (1990))). Boxes indicate codons within gp70 that encode different amino acids in 10A1 and 4070A viruses and that determine the different receptor utilization patterns of the two viruses. The Env start codon and the beginning of the mature gp 70 Env protein produced following cleavage of the leader sequence are indicated by arrows.

DESCRIPTION OF THE SPECIFIC EMBODIMENTS

Figure 1:
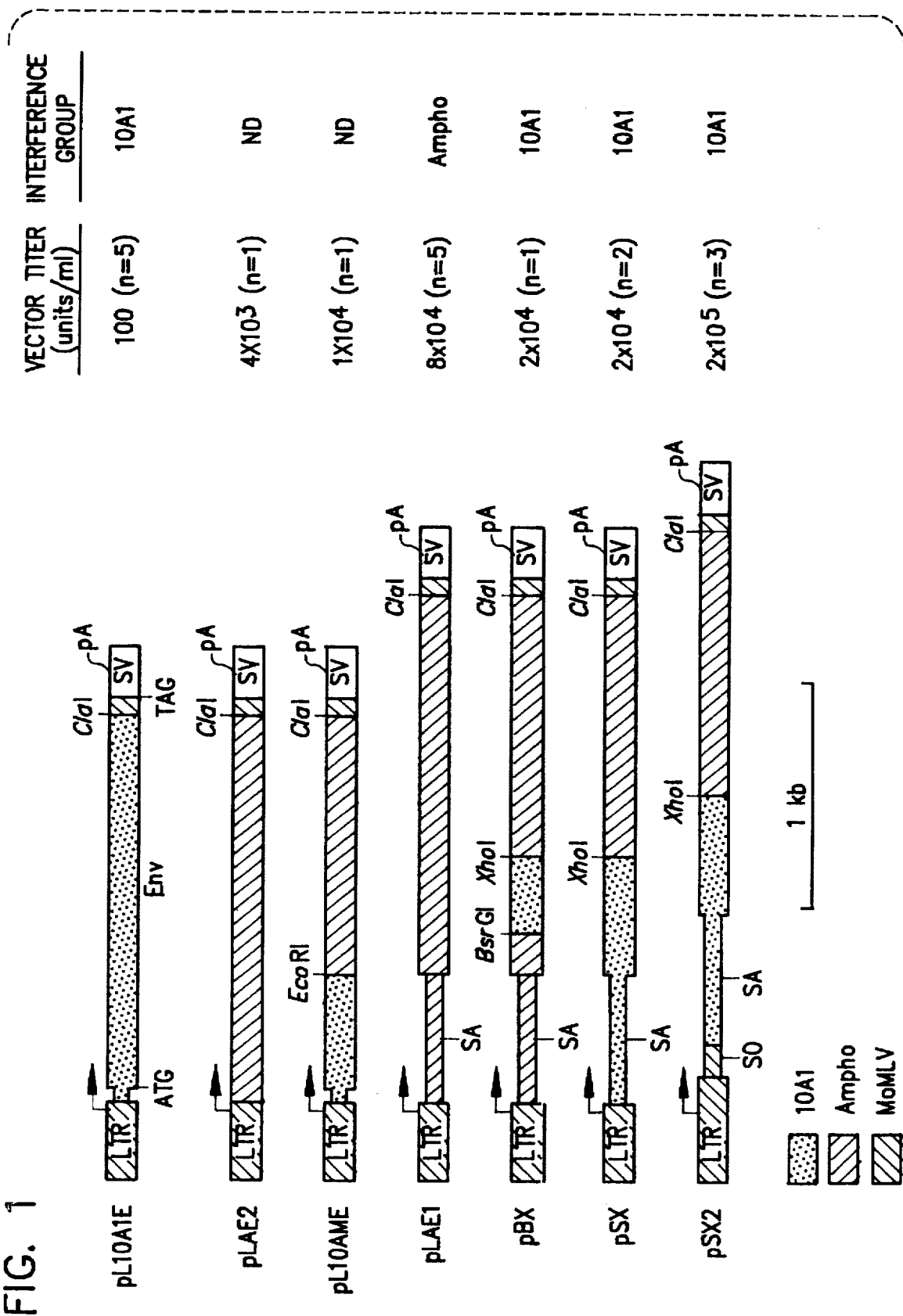
FIG. 1 shows Env expression constructs and their characterization.

The present invention provides retrovirus packaging cell lines based on the 10A1 class of retrovirus. 10A1 packaging cells have the advantages of the best amphotropic packaging cells, but also produce vectors capable of using an alternative receptor (Glvr-1) for cell entry. Utilization of Glvr-1 in mouse cells is efficient, and may be useful for gene transfer studies in mice where, e.g., no other retrovirus is known to use the mouse homolog of Glvr-1 for entry, including GALV itself. Use of Glvr-1 as a receptor for 10A1 pseudotype vector entry is less efficient in some human cell types, although Glvr-1 may be used efficiently for 10A1 vector entry in other human cell types, either due to higher levels of Glvr-1 expression or differences in post translational modifications in other cell types. Thus, the 10A1 pseudotype packaging cells are useful in methods of mammalian and particularly human gene transfer.

The 10A1 pseudotype packaging cells are a stable and reproducible source of high titer retroviral particles. 10A1 pseudotype packaging cell lines produce retroviral vectors at high titer (up to $10^5$–$10^7$ FFU/ml or greater) from populations of vector-transduced packaging cells. Clones may be isolated from these populations that produce even higher titer. The packaging cell lines of the invention can be selected and cloned for other desirable properties, such as stability of in vivo growth, lack of production of helper virus, lack of reinfection by viral particles packaged in the cell, stability from genetic rearrangement and recombinational events, resistance to complement lysis, and improved ability to infect cells from higher mammals. The replication defective virus vectors produced by the 10A1 packaging cell lines of the present invention permit the transfer of a wide variety of heterologous nucleic acid segments.

The packaging cell line is transduced or transfected with a replication defective virus vector, or a DNA construct having a strand corresponding to or complementary to a replication defective viral vector, containing the heterologous gene(s) of interest.

Representative genes useful in the present invention include, among others, those which encode, for example, blood clotting factors, adenosine deaminase (and especially human adenosine deaminase), interleukins, interferons, GM-CSF, G-CSF, erythropoietin and other cytokines, receptors, CFTR, tumor suppressor genes, antisense RNAs, and vaccine antigens. The vector comprises a sequence capable of providing retroviral long terminal repeats (LTRs), a sequence required for reverse transcription, a retroviral packaging sequence, and the gene sequence of interest. A DNA construct includes the LTRs necessary for host cell genome incorporation and expression. Following synthesis the viral DNA is integrated into cellular DNA so that the ends of the LTRs are directly joined to cellular sequences to form a stable structure (e.g., the provirus). The vector component necessary for reverse transcription does not necessarily include sequence coding for reverse transcriptase, but rather, includes a replication initiation site. A packaging signal, preferably specific for the retroviral vector of interest, is included in the vector. Donor and acceptor splice sites may also be present in the replication defective virus vectors. The splice sites enable the expression of additional heterologous inserted nucleic acid sequences.

To minimize the chance of producing infectious viral particles once the retroviral vector DNA is integrated into host cellular DNA, the replication defective virus vector need not include one or more of the sequences corresponding to the viral genes gag, coding for the viral core proteins, pol, coding for the viral RNA-dependent DNA polymerase (reverse transcriptase), or env, coding for the viral envelope proteins. The sequences can be omitted or rendered defective by mutagenesis.

For gene transcription from the replication defective virus vectors packaged by a 10A1 cell line of the present invention, the gene of interest may be linked to a heterologous promoter. The selection of a suitable promoter is well within the level of ordinary skill in the art. A wide variety of promoters have been described in the literature including both viral and cellular promoters. Viral promoters include the immediate early cytomegalovirus promoter (Boshart et al., *Cell* 41: 521–530, 1985), the MLV LTR promoter (Weiss et al., *RNA Tumor Viruses*, Cold Spring Harbor Laboratory Press, Cold Spring Harbor, N.Y., p766 (1985)) the SV40 promoter (Subramani et al., *Mol. Cell. Biol.* 1: 854–864, 1981) and the like. Cellular promoters include but are not limited to the mouse metallothionien-1 promoter (Palmiter et al., U.S. Pat. No. 4,579,821). Alternative splicing may also be exploited to facilitate the expression of polycistronic genes in the vector. In this strategy, one of the proteins encoded by the vector is translated from the full length vector RNA while partial splicing from a splice donor site near the 5' LTR to a splice acceptor just upstream of a downstream gene yields a transcript that encodes the downstream gene product. Because vector replication involves an RNA intermediate, construction of the vector containing inserted gene(s) should permit full-length transcription of vector genome.

The replication defective retrovirus vector particles packaged by the 10A1 cell lines in accordance with the present invention will often contain at least one exogenous (heterologous) gene. Heterologous genes encompass DNA (or RNA corresponding to the DNA) encoding proteins or peptides of interest and RNA molecules such as antisense RNA. DNA sequences encoding proteins of interest include genes, cDNAs and minigenes. For use in gene therapy, a retroviral vector will contain the heterologous gene or other DNA which is desired to be transferred to the cells of the intended recipient. Heterologous genes can code for the replacement or substitute of a defective or missing enzyme or other protein, RNA molecule or ribozyme in the patient, or encode therapeutic proteins or RNA molecules normally not present in the patient. The enzyme or other protein may function within a cell, or may be secreted and circulate in the body, such as hormones and blood factors. Genes which code for proteins whose levels do not have to be precisely controlled, and/or genes which cause disease by virtue of a single defect, are particularly suitable for insertion in a retroviral vector packaged by a 10A1 packaging cell line of the present invention.

Selectable markers can also be included in the replication defective retroviral vectors packaged according to the present invention, for investigative or experimental purposes, or to provide a means to select for cells containing the replication defective retroviral vectors. These markers include the neomycin and hygromycin phosphotransferases genes that confer resistance to G418 and hygromycin, respectively. Other markers include the mutant mouse dihydrofolate reductase gene (dhfr*) which confers resistance to methotrexate, the bacterial gpt gene which allows cells to grow in medium containing mycophenolic acid, xanthine, and aminopterin, the bacterial hisD gene which allows cells to grow in medium without histidine but containing histidinol, and the multidrug resistant gene (mdr) which confers resistance to a variety of drugs. These markers are dominant selectable markers and allow chemical selection of most cells expressing these genes.

Suicide genes may also be contained within the vectors packaged by the 10A1 cell lines of the present invention. Such genes provide a means to selectively kill cells containing the retroviral RNA. For example, the tk gene (Culver et al., *Science* 256: 1550–1552 (1992)) may be used in combination with gancyclovir to selectively kill transduced cells.

The exogenous gene for insertion in the vector can be an intronless cDNA copy of an mRNA encoding a gene product of interest. Large inserts can be placed in the replication defective retroviral vectors, but generally the gene(s) of interest and any attendant regulatory sequences should be no more than up to approximately 8 to 11 kb in size. The 5' and 3' noncoding regions of the cDNA can be trimmed to reduce the size of the insert and to remove potential polyadenylation signals that may occur in the 3' end of cDNAs. It may be preferable to insert the cDNA in the same transcriptional orientation as the viral LTR. Antisense RNAs can be expressed by reversing the orientation of the cDNA with respect to a promoter. Other inserts include intronless "minigenes" which are normal genes from which the introns have been removed. Entire genes containing introns can also be inserted, and typically will be inserted in reverse orientation to prevent removal of the introns during vector replication.

Although the 10A1 packaging cell lines produce retroviral vectors at relatively high titer, the vectors so produced can also be used at low titer, e.g., less than about $10^5$ cfu/ml, although higher titers of vector are often desirable, such as when a large number of cells must be infected. High titers may be in the range of $10^6$ to $10^7$ or more.

Packaging cell lines of the present invention may be constructed and optimized using a variety of strategies. In general, such strategies are designed to reduce the chance of recombination between helper construct (i.e., one or more constructs that provide trans-acting proteins required for production of replication defective retroviral vector particles) and vector that may result in the production of helper virus. In this context "helper virus" means undesirable infectious retrovirus produced from the integrated proviral genome in some packaging cells by genetic recombination and repair of the defective retroviral vector proviral genome. Strategies include but are not limited to helper constructs in which the packaging signal(s) have been deleted, helper constructs in which the gag, pol and env genes are split into two or more separate transcriptional units, e.g., containing gag-pol and env, or helper constructs in which the gag-pol and env genes are split into two separate transcriptional units and which contain mutations (e.g., by insertions of linkers) and deletions in the gag-pol and env transcriptional units. In addition, the 3' LTRs in separate transcriptional units can be replaced with polyadenylation signals from SV40, thereby requiring an additional recombinational event to generate helper virus. Avoidance of homologous overlap between vector and helper virus sequences in the 10A1 packaging cells decreases the chance of helper virus production. This can be accomplished by removing as much of the helper virus sequences from the vector as possible. Suitable helper constructs are cotransfected with the vector of the present invention thus providing the required trans-acting proteins and allowing virus particle production. Trans-acting proteins may also be provided by packaging cell lines that are designed to provide all viral proteins but not to package or transmit the RNAs encoding these functions. These packaging cell lines contain the replication defective retroviral vector genome of interest, and expression of the trans-acting proteins permits the production of packaged retroviral vectors. For the construction of packaging cell lines suitable for use in the present invention, the trans-acting viral proteins may be provided in a transient or inducible manner. Trans-acting viral genes may be placed under the control of an inducible promoter such as the tetracycline-responsive promoter (Gossen and Bujard, *Proc. Natl. Acad. Sci. USA* 89: 5547–5551, 1992 and Pescini et al., *Biochem. Biophys. Res. Comm.* 202: 1664–1667, 1994). For packaging cell lines containing trans-acting genes under the control of regulated promoters, packaging may be induced by inducing the promoter.

Cells suitable for use in preparing packaging cell lines of the present invention are derived from vertebrates and include, for example, avian, primate, porcine, human, murine, canine etc. Particularly preferred cells for preparing packaging cells are NIH 3T3, however, other suitable cells are readily available.

The 10A1 packaging cells are produced by introducing DNA constructs which direct the expression of trans-acting gag, pol and 10A1 envelope proteins that are required for packaging replication defective retroviral particles. Methods for introducing such constructs include, for example, calcium phosphate precipitation (Wigler et al., *Cell* 14: 725, 1978; Corsaro and Pearson, *Somatic Cell Genetics* 7: 603, 1981; Graham and Van der Eb, *Virology* 52: 456, 1973); lipofection (Felgner et al., *Proc. Natl. Acad. Sci. USA* 84: 7413–7417, 1987), microinjection and electroporation (Neumann et al., *EMBO J.* 1: 841–845, 1982). The cells can also be transduced with virus, such as SV40, CMV and the like. In the case of viral vectors, cloned DNA molecules may be introduced by infection of susceptible cells with viral particles. The gag and pol genes may be derived from a wide variety of oncoviruses, including retroviruses, and within a preferred embodiment the gag and pol genes are derived from an amphotropic murine leukemia virus (MuLV). Suitable env genes include the 10A1 env gene (though the expression plasmid pL10A1 E containing the complete 10A1 env gene had low activity in a transient assay for Env function), and preferably a chimeric env gene which is comprised at least of a sequence encoding the residues that are encoded within the 376 base pair BsrGI-XhoI fragment of the 10A1 env gene that confer 10A1 receptor use pattern. The non-10A1 portion of a chimeric, or hybrid, env gene comprises an amphotropic env gene having at least the native sequences that are analogous to the sequences encoding the residues encoded within the 376 base pair BsrGI-XhoI fragment of the 10A1 env gene that confer 10A1 receptor use replaced with the analogous fragment(s) of the 10A1 env gene. In one embodiment the chimeric env gene is an amphotropic env gene in which the 5' coding sequence from the translation start to the XhoI site is replaced with the analogous fragment of the 10A1 env gene.

Using the 10A1 packaging cell lines of the present invention, replication defective retroviral vectors are assembled into corresponding retroviral particles by surrounding the recombinant viral RNA with the gag and pol proteins to form a core particle and encapsulating the core particle in a membrane containing the env encoded protein. Thus, a packaging cell of the present invention provides replication defective retroviral particles capable of transducing cells (i.e., an infectious virus having a ribonucleoprotein core particle surrounded by a membrane containing 10A1 envelope protein) containing the vectors as described herein.

The production of undesirable helper virus can be detected in a variety of ways, including, e.g., vector rescue assays in which cells containing but not producing a selectable replication-defective viral vector are transduced with the test virus and assayed for production of the vector. Rescue of the vector can be detected by passaging the cells to allow virus spread and assaying medium exposed to these cells for the selectable viral vector in a standard colony assay. Another method for detecting helper virus utilizes FAB cells (Yu and Linial, *J. Virol.* 67: 6618–6624 (1993). In this method, conditioned medium is exposed to the FAB cells and the presence of helper virus is detected by the induction of blue coloration in cells transduced with virus expressing bell. Representative assays include the $S^+L^-$ assay described by Bassin et al. (*Nature* 229: 5646, (1971), incorporated herein by reference) and marker rescue described by Miller et al. (*Meth. Enzymol.* 217: 581–599 (1993), incorporated herein by reference).

The replication defective retroviral vectors packaged by the 10A1 packaging cell lines of the present invention provide the means for gene transfer in a wide range of animals species, including, e.g., experimental and domestic animals, livestock, birds, etc. The 10A1 retrovirus is the result of a recombination between 1504A amphotropic virus and an endogenous provirus found in Swiss mice. Rasheed et al., *Int. J. Cancer* 29:345–350 (1982), incorporated herein by reference. 10A1 virus exhibits the wide host range characteristic of the parent amphotropic retrovirus but also infects amphotropic virus-resistant CHO cells and can use alternate receptors, either Ram-1 or Glvr-1, in different cell types. Thus the recombinant viruses produced according to the methods of the invention have the same host range. The replication defective vectors produced by a packaging cell of the present invention are useful in gene transfer in, for example, birds (e.g., chickens), sheep, cows, horses, cats, rats, mice, hamsters, dogs, monkeys and primates (e.g., chimpanzees, macaques,and monkeys, and humans). For livestock uses, for example, the particles produced according to the invention are useful for infecting cells in preimplantation embryos, which embryos when implanted in an animal creates a transgenic animal or an animal which expresses a gene product that it would normally not produce.

The replication defective retroviral particles packaged in a 10A1 packaging cell line of the invention are used to infect (transduce) target cells, such as, for example, those which are defective in expression of the gene of interest, or which can act to secrete the desired protein. By transduction is meant the process by which non-viral genes are transferred and expressed in a host cell by a viral vector. The infection (transduction) can take place ex vivo or in vivo. When the infection is ex vivo, typically the targeted cells, e.g., lymphocytes, bone marrow and hematopoietic stem cells, fibroblasts, hepatocytes, endothelial cells, benign or malignant tumor cells, etc., are autologous in that they have been removed from the individual in need of the gene product of interest, but allogeneic or even xenogeneic cells may also be employed. The cells are infected by the replication defective virus particles containing the gene of interest, and the cells are returned (or transplanted) to the host. When the transduction of the host cells is ex vivo, typically medium containing the recombinant replication defective virus particles is incubated with the target cells. The target cells may be cultivated in vitro to expand their numbers in primary cell cultures. Transduction is typically during the early days of host cell culture, and may be accomplished by co-cultivating the target cells with a cell line producing replication defective virus vectors. The target cells are not necessarily cultured prior to transduction and replacement in the host patient.

For in vivo transduction, the replication defective virus particles can be administered to the host in a wide variety of ways. The particular mode of administration will depend upon several factors, including, among others, the particular use intended, the host being treated, the tissue targeted for transduction, the gene product of interest, the general health of the patient, etc., but will generally be administered intradermally, subcutaneously, intramuscularly, topically (e.g., aerosol, such as via a nebulizer), intravenously, intraperitoneally, or the like. Thus, the vectors may be administered to tissues and organs (e.g., via a catheter) such as the lungs, bladder, urethra, uterus, liver, heart and circulatory system, kidney, bone marrow, brain, lymphoid tissues, stomach, small intestine, large intestine, colon and prostate.

The dosages of the replication defective virus vectors produced according to the invention will be determined through empirical experiments such as dose escalation studies and the like. It must be kept in mind that the materials of the present invention may be employed in serious disease states, that is, life-threatening or potentially life threatening situations. In such cases, in view of the ability of the replication defective virus particles produced by the present invention to infect a wide variety of vertebrate cells, it is possible and may be felt desirable by the treating physician to administer substantial excesses of these viral particles.

The following examples are offered by way of illustration, not by way of limitation.

EXAMPLE I

Construction and Function of Chimeric 10A1 Envelope Expression Vectors

To make retrovirus packaging cells for production of vectors with a 10A1 pseudotype, 10A1 Env expression plasmids were constructed. 10A1 Env and hybrid Env expression plasmids were tested by introducing the plasmids into LGPS cells that contained a retroviral vector and measuring the titer of vector produced.

Cell Culture. NIH 3T3 thymidine kinase deficient (TK$^-$) cells (Miller et al., *Mol. Cell. Biol.* 6:2895–2902 (1986)), 208F rat embryo fibroblasts (Quade, *Virol.* 98:461–465 (1979)), 293 adenovirus-transformed human kidney cells (Graham et al., *J. Gen. Virol.* 36:59–72 (1977)), PA317 amphotropic retrovirus packaging cells (Miller, id.), and PE501 ecotropic retrovirus packaging cells (Miller et al., *BioTechniques* 7:980–990 (1989); ecotropic viruses are those which are able to infect only rodent cells) were grown in Dulbecco's modified Eagle's medium with 10% fetal bovine serum. PG-4 Moloney murine sarcoma virus-infected G355 cat cells (Dunn et al., *J. Virol.* 67:4704–4711 (1993)) were grown in McCoy's medium with 15% fetal bovine serum.

Replication-competent retroviruses. The pB6 plasmid contains a circularly permuted clone of the 10A1 retrovirus (Ott et al., *J. Virol.* 64:757–765 (1990), incorporated herein by reference) (obtained from Dr. A. Rein, NCI-Frederick Cancer Research and Development Center, Frederick, Md.). The pB6 plasmid was cut with SalI to release the 10A1 segment, religated at low DNA concentration to recircularize the 10A1 virus, and introduced into NIH 3T3 (TK$^-$) cells by Ca$_2$PO$_4$-mediated transfection. The cells were passaged for 2 weeks to allow complete virus spread, and were than used in interference assays and to make 10A1 helper virus for infection of other cells. The plasmid pAM (Miller et al., *Mol. Cell. Biol.* 5:431–437 (1985)) contains a hybrid amphotropic retrovirus constructed by replacing the env gene of MoMLV (Shinnick et al., *Nature* 293:543–548 (1981)) with that of 4070A amphotropic virus (Chattopadhyay et al., *J. Virol.* 39:777–791 (1981)). NIH 3T3 (TK$^-$) cells were transfected with pAM, passaged for two weeks to allow complete virus spread, and were then used in interference assays and to produce amphotropic helper virus for infection of other cells. Mv 1 Lu mink cells (ATCC CCL 64) producing gibbon ape leukemia virus (GALV) SEATO strain were obtained from Dr. M. Eiden, National Institutes of Health, Bethesda, Md., and were used to produce GALV for infection of other cells.

As shown in FIG. 1, each Env expression plasmid contained: an MoMLV LTR promoter (transcription start site indicated by an arrow) truncated at the 5' end to a Sau3AI site just upstream of the transcriptional enhancers in the LTR, the Env coding region, the early polyadenylation signal (pA) from SV40 inserted just after the Env stop codon, and plasmid sequences (not indicated) derived from the poison-minus plasmid pML-1 (Lusky et al., *Nature* 293:79–81 (1981)). LTR/env junctions were SmaI/BsrBI for pL10A1E and pL10AME, SmaI/PflMI (blunted) for pSX2.

Functional activity of the chimeric envelope expression constructs, pL10A1E and pL10AME, were transfected into the LGPS clone 91-22 (U.S. Pat. No. 5,470,726, incorporated herein by reference) that had been previously infected with the retroviral marker vectors LNL6 (Bender et al., *J. Virol.* 61:1639–1646 (1987)) or LAPSN (Miller et al., *Proc. Natl. Acad. Sci. USA* 91:78–82 (1994)) (yielding LGPS/LNL6 and LGPS/LAPSN) by using helper-virus free vectors made by PA317 cells. The LNL6 and LAPSN vectors contained the neomycin resistance gene or the alkaline phosphatase gene, respectively, flanked by retroviral LTR's. The cells LGPS/LNL6 and LGPS/LAPSN express the gag and pol genes, but do not contain the env gene required to produce functional vectors. As a control for viral vector production, an irrelevant plasmid was transfected into each cell line. One day post-transfection the culture medium was changed. The culture medium from each transfection was harvested at two days post-transfection. As an additional control, untransfected LGPS/LNL6 and LGPS/LAPSN were cultured under the same conditions and medium from each culture was harvested at day two.

The harvested media were used in transient rescue assays to determine whether functional vector was produced from the transfected cells. Target NIH 3T3 cells were seeded at 10$^5$ per 6 cm dish or at 5×10$^4$ per 35 mm (diameter) well of a 6 well plate on day 1, the cells were fed with fresh medium containing 4 μg Polybrene (Sigma) per ml and media from the LGPS/LAPSN-transfected or LGPS/LAPSN-nontransfected cells were added on day 2. The cells were fixed with glutaraldehyde and stained for alkaline phosphatase expression as described (Fields-Berry et al., *Proc. Natl. Acad. Sci. U.S.A.* 89:693–697 (1992)) on day 4. Assay for the neo expression vector LNL6 was identical except that instead of staining for AP, the medium was changed to medium containing 0.75 mg/ml G418 (active) on day 3 and G418-resistant colonies were stained with Coomassie Brilliant Blue G (Sigma; 1 g/liter in 40% methanol-10% acetic acid) on day 8. Vector titers are averages with the number of replicate assays indicated. Independent titer determinations varied no more than 3-fold from the average. Vector titer was <1 unit per ml when the LGPS/LASN and LGPS/LNL6 was transfected with no DNA or the irrelevant plasmid was used for transfection.

The vectors produced from the LGPS/LAPSN+pL10A1E and LGPS/LAPSN+pLAE1 cells were subjected to interference analysis. Interference grouping was determined by titering the vectors on NIH 3T3, NIH 3T3/AM-MLV and NIH 3T3/10A1 cells. Plasmid pLAE1 was used as a positive control for the production of an amphotrophic vector and contains an amphotrophic env gene flanked by retroviral LTRs (FIG. 1). The vectors produced from the pL10A1E-transfected LPGS/LAPSN cells were shown to be in the 10A1 interference group and gave equivalent titers (within 2-fold) on NIH 3T3 and NIH 3T3/AM-MLV cells. The vector in the amphotrophic interference group (pLAE1) had a titer on NIH 3T3 cells that was >10$^4$ higher than that measured on NIH 3T3/AM-MLV cells. Vector titers measured on NIH 3T3/10A1 cells were <2 units/ml for all vectors tested for interference grouping.

A 10A1 Env expression plasmid, pL10A1E, was initially designed to minimize or eliminate overlap of sequences in the construct with those present in retroviral vectors or in the Gag-Pol expression vector. The Env expression plasmid pL10A1E (FIG. 1) had no homologous overlap at the 3' end with standard retroviral vectors (Miller et al., BioTechniques 7:980–990 (1989)) and minimal overlap at the 5' end with the 3' end of the MoMLV pol gene present in the Gag-Pol Pol expression plasmid. Surprisingly, this construct had poor activity in the transient assay for Env function compared to a similar plasmid encoding an amphotropic Env protein, pLAE2 (FIG. 1). Analysis of the pL10A1E plasmid with multiple restriction enzymes showed band patterns indicating the plasmid had the correct structure, but the entire Env coding region has not been sequenced to check for possible subtle defects. Two independent plasmid clones were tested with similar results. Note that the carboxy ends of all of the Env constructs (3' of the ClaI site, FIG. 1) consisted of MoMLV env sequences, but this did not affect the interpretation of the results because the amino acid sequence in this region is identical for the MoMLV, 10A1 and amphotropic 4070A viruses.

A hybrid Env expression plasmid consisting of the amino terminus of the 10A1 Env protein fused to the carboxy terminus of the 4070A amphotropic Env at a common EcoRI site (Ott et al., J. Virol. 66:4632–4638 (1992)), pL10AME, performed at least as well as the amphotropic Env construct in the transient vector rescue assay (FIG. 1). Preliminary work indicated that the vector made with the pL10AME plasmid had the receptor utilization properties of 10A1. These results indicated that there was some defect in the 3' end of the 10A1 env gene. However, it was possible to make high-titer virus by using the original 10A1 helper virus plasmid, so either the defect was not severe or it can be repaired during helper virus replication.

An amphotropic Env expression plasmid, pLAE1 (FIG. 1), that incorporated the region that normally lies upstream of the env gene in the retrovirus produced a higher vector titer in the transient vector rescue assay. Two similar constructs in which the critical regions in the amino terminus of the amphotropic Env were replaced with 10A1 sequences (pBX and pSX) also gave a higher titer, although not as high as the amphotropic construct pLAE1 (FIG. 1). Vectors made with the pBX construct, in which only the BsrGI to XhoI region of the amphotropic env gene was replaced with 10A1 sequences, or vectors made with the pSX construct, had 10A1 interference properties (FIG. 1).

One other construct (pSX2; FIG. 1) included the splice donor present after the retroviral LTR that is normally used with a splice acceptor just upstream of env in murine leukemia viruses to generate the spliced env mRNA. This construct produced the highest vector titer of all constructs tested in the transient vector rescue assay.

In summary, while high titer vectors were not achieved by using the wild-type 10A1 env sequences, such vectors were made by using hybrid 10A1/amphotropic constructs. The highest vector titers were obtained by including the retroviral splice donor and acceptor sequences that are normally used to make the spliced retroviral env mRNA.

EXAMPLE II

Generation of 10A1-Pseudotype Retrovirus Packaging Lines

To generate stable retrovirus packaging cells that expressed the hybrid 10A1 Env protein, plasmids were introduced into cells of LGPS clone 91-22 that express MoMLV Gag-Pol proteins. LGPS cells were made by cotransfection of an MoMLV Gag-Pol expression vector with the herpes simplex virus TK gene into NIH 3T3 TK⁻ cells followed by selection of the cells in medium containing hypoxanthine, amethopterin, and thymidine (HAT medium). The best Env expression construct (pSX2) was introduced into LGPS cells by cotransfection (Miller et al., BioTechniques 7:980–990 (1989)) with either a mutant methotrexate-resistant dihydrofolate reductase gene (dhfr*) contained in the plasmid pFR400 (Simonsen et al., Proc. Natl. Acad. Sci. USA 80-2495–2499 (1983)) or with a hygromycin phosphotransferase (hpt) gene contained in the plasmid pSV2 Δ13-hyg (obtained from Paul Berg, Stanford University). The ratio of selectable marker plasmid to Env expression plasmid was 1:20 or 1:100. Cell colonies containing the genes were selected in 100 nM methotrexate with dialyzed fetal bovine serum or 0.4 mg/ml hygromycin respectively, and were isolated using cloning rings. Cells lines were generated with either marker so that a 10A1 packaging cell line was available for use with any dominant marker. Clone designations begin with PT (Packaging cells having a "Ten" A1 pseudotype), followed by a number from 1–74 for clones cotransfected with dhfr*, or from 100–125 for clones cotransfected with hpt.

Two methods were used to screen packaging cell clones for their ability to produce a retroviral vector. The first method involved introduction of the LAPSN vector into the cells by calcium phosphate-mediated transfection followed by assay of virus production two days after transfection (transient vector rescue). Later assays were simplified by eliminating the transfection step and introducing the LAPSN vector by exposing the cells to LAPSN vector made by PE501 cells (MOI≈1) (transduction by ecotropic pseudotype vectors produced from PE501 cells is unaffected by expression of the 10A1 Env or MoMLV Gag-Pol proteins). Vector titer was measured 2 days after LAPSN transduction. The titers of LAPSN vector produced by either technique were similar.

Fifty-six dhfr* and seventeen hpt cotransfected cell clones were analyzed for vector production. The titers of vector produced were similar from packaging cell clones made by using either marker or by using either ratio of selectable marker plasmid to pSX2 Env plasmid (1:20 or 1:100). LAPSN titers up to $10^6$ per ml were made from some packaging cell clones in this transient virus production assay.

Seven of the best dhfr*-cotransfected packaging cell clones were chosen for further analysis. The cells were transduced with LAPSN(PE501) vector and selected in G418 for 5 days to ensure the presence of the LAPSN vector in every cell. LAPSN vector titers produced from these packaging cell clones ranged from $2 \times 10^6$ to $10^7$ FFU/ml.

LAPSN vector preparations from three of these cell lines (PT28/LAPSN, PT42/LAPSN, and PT67/LAPSN) were analyzed for receptor use in NIH 3T3 cells. LAPSN vector from all three clones could use a receptor other than the amphotropic receptor for cell entry, and the interference properties of LAPSN vectors produced by these packaging cells closely matched those of LAPSN vectors produced by using 10A1 helper virus to pseudotype the vector (Table 1). The 10A1-based retrovirus packaging cell line PT67 has been deposited with the American Type Culture Collection, 12301 Parklawn Drive, Rockville, Md. 20852 USA, on Feb. 5, 1987, as ATCC CRL-12284.

TABLE 1

The LAPSN vector produced by 10A1-pseudotype packaging cells can use a receptor other than the amphotropic receptor for entry into NIH 3T3 mouse cells.[a]

| LAPSN pseudotype | Vector titer (FFU/ml) on the following target cells: | | |
|---|---|---|---|
| | 3T3 | 3T3 + AM – MLV | 3T3 + 10A1 |
| PT28 | $2 \times 10^6$ | $1 \times 10^6$ | 40 |
| PT42 | $2 \times 10^6$ | $8 \times 10^5$ | 40 |
| PTG7 | $3 \times 10^6$ | $2 \times 10^6$ | 90 |
| 10A1 | $3 \times 10^7$ | $2 \times 10^7$ | 500 |
| PA317 | $1 \times 10^7$ | 30 | 20 |
| PE501 | $2 \times 10^6$ | $1 \times 10^6$ | $1 \times 10^6$ |

[a]Values are average results from duplicate assays in a single experiment which varied by no more than 21% from the average (except for the value of 20 where the numbers of colonies per plate were low and varied by 47% from the average). The experiment was performed once.

LAPSN vector preparations from these three packaging cell lines were also analyzed for the presence of replication-competent retrovirus by using the PG-4 S$^+$L$^-$ assay and a marker rescue assay.

To perform the PG-4 S$^+$ L$^-$ helper virus assay, PG-4 cells were seeded at $10^5$ per 6 cm (diameter) dish on day 1, the cells were fed with fresh medium plus 4 µg Polybrene per ml and test virus was added on day 2, and foci were counted on day 7. To perform the marker rescue assay for helper virus, NIH 3T3 cells were plated at $10^5$ per 6 cm dish on day 1, the cells were fed with fresh medium plus 4 µg Polybrene per ml and 0.5 ml of test virus containing the LAPSN vector on day 2, the cells were trypsinized and split 1:10 every 2 to 3 days for 2 weeks while keeping the cells at high density to facilitate potential virus spread, confluent dishes of cells were fed on day 15, and medium was harvested from the cells. The medium was used to infect fresh NIH 3T3 cells on day 16 and the cells were stained for AP$^+$foci two days after infection. The passaged cells were also stained for AP to ensure that the cells had been transduced with the LAPSN vector, and therefore were capable of producing the vector if helper virus were present, and cells were 20 to 100% AP positive in these assays.

Use of the PG-4 S$^+$ L$^+$ assay was complicated by significant PG-4 cell fusion following exposure of cells to more than 50 µl of medium from the packaging cells, making it difficult to distinguish helper virus-induced foci from areas of cell death due to cell fusion. However, 50 and 10 µl samples of the LAPSN vector preparations induced no foci in the PG-4 S$^+$L$^-$ assay, indicating a helper virus titer of <20 FFU/ml, while 10A1 virus produced by NIH 3T3 cells gave a titer of $4 \times 10^6$ FFU/ml in the same assay.

The LAPSN vector preparations were also for the presence of helper virus using a marker rescue assay. In this case, cell fusion induced by large amounts of the LAPSN vector did not complicate the assay. Duplicate 0.5 ml samples of vector from PT28/LAPSN, PT42/LAPSN, and PT67/LAPSN cells scored negative for helper virus in this assay, indicating the absence of helper virus (<1 per ml) in the LAPSN preparations from the three clones tested.

EXAMPLE III

The Pol/Env regions of 10A1 and 4070A viruses were sequenced from a common SphI site in the 3' end of the pol gene to the EcoRI site in the env gene (10A1) or the Pf/MI site just upstream of the Env start codon (4070A). Sequence analysis was performed to confirm the amino acid sequence in 10A1 responsible for its ability to use multiple receptors, and to define the previously unsequenced region of the pol genes of 10A1 and 4070A present in the Env expression plasmids.

DNA fragments to be sequenced were cloned into Bluescript II (Stratagene, La Jolla, Calif.) and double-stranded plasmid DNA was prepared. Sequencing was performed on both strands of the insert by the dideoxy sequencing method using M13 dye primers and Sequenase DNA polymerase to cycle the reaction (PRISM kit, Applied Biosystems, Foster City, Calif.) and an Applied Biosystems 373A DNA sequencer and sequence analysis software. Sequences were compiled using a text editor and checked for accuracy against the primary fluorescent dye profile data. These sequences were compared to that of MoMLV (FIG. 2).

The sequence of the 10A1 env region was different from the published sequence (Ott et al., *J. Virol.* 64:757–765 (1990)) at 7 bases (circled in FIG. 2), none of which resulted in changes to the previously predicted amino acid sequence of the gp70 protein, although 3 changes at bases 719–721 (FIG. 2) did change a predicted amino acid in the Env leader peptide. There are only 6 amino acid differences between 10A1 and 4070A viruses in the BsrGI to XhoI region of Env (boxed codons in FIG. 2). Because the pBX Env expression construct had a 10A1 receptor use pattern (FIG. 1), these changes are responsible for the difference in receptor use between 10A1 and 4070A viruses as shown by Ott et al., *J. Virol.* 66:4632–4638 (1992).

The 10A1 and 4070A virus sequences are similar upstream of env with scattered base differences and a 3 b.p. insertion in 10A1 at bases 615–617. Relatively long regions of identity between 10A1 and MoMLV upstream of env raise the possibility of recombination in this region to join the gag-pol and env sequences present in the 10A1 pseudotype packaging cells, which might facilitate helper virus production, but additional recombination events would still be required to regenerate the viral LTRs.

EXAMPLE IV

GALV Receptor Utilization by a 10A1 Pseudotype Vector

One aspect of this invention relates to producing retroviral vectors capable of using either the Ram-1 or Glvr-1 receptors for entry into human and other cell types. Initial studies with vectors produced in the Env expression plasmid transfection studies indicated that 10A1 pseudotype vectors might not effectively use the Glvr-1 receptor in 208F rat cells. Interference studies in 208F rat cells were then performed. Wild-type 10A1 virus was used instead of the 10 A1 packaging cells to rule out any effect of MoMLV and 4070A virus sequences present in the 10A1 packaging cells.

As shown in Table 2, LAPSN(10A1) vector efficiently transduced 208F cells and 208F cells previously infected with GALV, but only poorly transduced 208F cells previously infected with AM-MLV amphotropic virus. An identical pattern was observed for amphotropic LAPSN(PA317) vector. In contrast, GALV pseudotype LAPSN(PG13) vector efficiently transduced 208F cells and 208F cells previously infected with AM-MLV amphotropic virus, but poorly transduced 208F cells previously infected with GALV. These results show that a 10A1 pseudotype vector cannot utilize the GALV receptor for entry into 208F rat cells.

TABLE 2

The LAPSN vector with a 10A1 virus pseudotype can use the amphotropic receptor, but not the GALV receptor, for entry into rat 208F cells.[a]

| LAPSN pseudotype | Vector titer (FFU/ml) on the following target cells: | | |
|---|---|---|---|
| | 208F | 208F + AM − MLV | 208F + GALV |
| 10A1 | $1 \times 10^7$ | 500 | $1 \times 10^7$ |
| PA317 | $2 \times 10^6$ | 200 | $2 \times 10^6$ |
| PG13 | $2 \times 10^5$ | $2 \times 10^5$ | 100 |

[a]Values are average results from duplicate assays in a single experiment which varied by no more than 14% from the average. The experiment was repeated two more times with similar results.

Interference analysis was used to determine the ability of 10A1 pseudotype LAPSN vector to use the GALV receptor in primary human fibroblasts (HFF) (Table 3). LAPSN (PA317) vector efficiently transduced HFF and HFF infected with GALV, confirming that GALV binds to a different receptor than that used by amphotropic virus for cell entry. Similarly, LAPSN(PG13) efficiently transduced HFF and HFF infected with amphotropic virus, and LAPSN(PG13) poorly transduced HFF infected with GALV, as expected due to receptor blockage.

TABLE 3

The use of amphotropic and GALV receptors for entry into human fibroblasts by a LAPSN vector with a 10A1 virus pseudotype.[a]

| LAPSN pseudo-type | Vector titer (FFU/ml) on the following target cells: | | | |
|---|---|---|---|---|
| | HFF | HFF + AM − MLV | HFF + GALV | HFF + 10A1 |
| PA317 | $2 \times 10^6$ | 2 | $2 \times 10^6$ | 2 |
| PG13 | $3 \times 10^5$ | $2 \times 10^5$ | 20 | $5 \times 10^4$ |
| 10A1 | $6 \times 10^6$ | $5 \times 10^3$ | $6 \times 10^6$ | 8 |

[a]Values are average results from duplicate assays in a single experiment which varied by no more than 10% from the average (except for values <10 where the numbers of colonies per plate were low and varied by up to 100% from the average). The experiment was repeated a second time with similar results.

These results confirm that GALV and amphotropic virus use different receptors for entry into human cells and thus show no interference. LAPSN(10A1) vector transduced HFF cells previously infected with amphotropic virus at a significantly higher rate than the amphotropic pseudotype LAPSN(PA317) vector did, but at lower efficiency than the LAPSN(10A1) vector transduced HFF or HFF cells previously infected with GALV. Also, GALV pseudotype LAPSN (PG13) vector transduction of HFF cells was significantly inhibited by previous infection with 10A1 virus. These results indicate that 10A1 pseudotype vectors can use the GALV receptor for entry into human cells, although perhaps not as efficiently as they use the amphotropic receptor.

Since the properties of 10A1 pseudotype vectors may differ for cells form different individuals or tissue sources, interference analyses were performed on additional human cell lines from different individuals and tissues. 293 embryonic kidney cells (Table 4) and IB3 airway epithelial cells (data not shown). In both cases the results were similar to experiments with HFF cells and indicate that 10A1 pseudotype vectors can use both Ram-1 and Glvr-1 for cell entry, but use the GALV receptor less efficiently.

TABLE 4

Use of the amphotropic and GALV receptors for entry into human 293 cells by LAPSN vector with a 10A1 virus pseudotype.[a]

| LAPSN pseudo-type | Vector titer (FFU/ml) on the following target cells: | | | |
|---|---|---|---|---|
| | 293 | 293 + AM − MLV | 293 + GALV | 293 + 10A1 |
| PA317 | $8 \times 10^4$ | 40 | $8 \times 10^4$ | 5 |
| PG13 | $2 \times 10^5$ | $2 \times 10^5$ | 20 | $1 \times 10^4$ |
| 10A1 | $3 \times 10^5$ | $8 \times 10^3$ | $3 \times 10^5$ | $2 \times 10^2$ |

[a]Values are average results from duplicate assays in a single experiment which varied by no more than 20% from the average (except for the value <10 where the numbers of colonies per plate were low and varied by 33% from the average). The experiment was repeated a second time with similar results.

In a separate experiment, interference analysis was performed using the same pseudotyped LAPSN vectors in NIH 3T3 cells (Table 5). Note that GALV does not infect mouse cells and therefore could not be tested. 10A1 virus blocked transduction by amphotropic pseudotype LAPSN(PA317) vector, showing that 10A1 binds to and presumably can enter cells by using the amphotropic receptor. LAPSN (10A1) vector had the same titer on NIH 3T3 cells or NIH 3T3 cells previously infected with AM-MLV, showing that a 10A1 pseudotype vector can enter cells by using a receptor other than the amphotropic receptor. Control experiments showed that transduction by ecotropic pseudotype (LAPSN (PE501) vector was blocked by MoMLV, but was unaffected by the presence of AM-MLV or GALV, and that the presence of MoMLV did not affect transduction by 10A1 or amphotropic pseudotype LAPSN vectors. The receptor used by ecotropic virus for cell entry is different from those used by 10A1 and amphotropic retrovirus. These results show that poor infection of NIH 3T3+10A1 cells by 10A1 or amphotropic pseudotype vectors is not due to a general problem with the cells, because an ecotropic vector efficiently transduces these cells, and that amphotropic pseudotype vector transduction is not blocked in all retrovirus infected NIH 3T3 cells, because the amphotropic LAPSN vector can efficiently transduce MoMLV infected cells.

TABLE 5

Use of a receptor other than the amphotropic receptor for entry into NIH 3T3 mouse cells by the LAPSN vector with a 10A1 virus pseudotype.[a]

| LAPSN pseudo-type | Vector titer (FFU/ml) on the following target cells: | | | |
|---|---|---|---|---|
| | 3T3 | 3T3 + AM − MLV | 3T3 + 10A1 | 3T3 + MoMLV |
| PA317 | $5 \times 10^6$ | 40 | 3 | $4 \times 10^6$ |
| 10A1 | $7 \times 10^6$ | $6 \times 10^6$ | $2 \times 10^2$ | $6 \times 10^6$ |
| PE501 | $3 \times 10^6$ | $2 \times 10^6$ | $2 \times 10^6$ | 40 |

[a]Values are average results from duplicate assays in a single experiment which varied by no more than 14% from the average (except for the value <10 where the numbers of colonies per plate were low and varied by 33% from the average). The experiment was repeated a second time with similar results.

These results and previous results showing that the mouse homolog of the human GALV receptor can function as a receptor for GALV pseudotype vectors in CHO cells (Miller et al., *J. Virol.* 68:8270–8276 (1994)) indicated that 10A1 pseudotype vectors can efficiently transduce NIH 3T3 mouse cells by using Glvr-1. Because 10A1 virus can block infection by an amphotropic vector, 10A1 can bind Ram-1 and can therefore use Ram-1 to enter mouse cells.

Although the foregoing invention has been described in some detail by way of illustration and example for purposes of clarity of understanding, it will be obvious that certain changes and modifications may be practiced within the scope of the appended claims.

What is claimed is:

1. A cultured packaging cell for producing a replication-defective retroviral vector particle, wherein the packaging cell is a vertebrate cell comprising:
   a first vector encoding a retroviral env protein comprising amino acid residues of a 10A1 retrovirus that direct binding of the retroviral vector particle to Glvr-1 or Ram-1 retroviral receptors on a target cell; and
   a second vector encoding retroviral gag and pol proteins, wherein said env, gag, and pol proteins are expressed in said packaging cell, and wherein upon the introduction of a third vector comprising a sequence encoding a heterologous protein of interest, a replication-defective retroviral vector particle is produced by assembly of said env, gag, and pol proteins, such that said vector particle binds to Glvr-1 and Ram-1 retroviral receptors of target cells.

2. The cultured packaging cell of claim 1, wherein said first vector encodes the 10A1 retrovirus env amino acid residues within the BsrGI-XhoI fragment of the 10A1 retrovirus env gene.

3. The cultured packaging cell of claim 1, wherein said first vector includes the nucleotide sequence of the BsrGI-XhoI fragment of the 10A1 retrovirus env gene.

4. The cultured packaging cell of claim 1, wherein the retroviral env protein is a chimeric protein having non-10A1 retrovirus env amino acid residues from a different amphotropic retrovirus.

5. The cultured packaging cell of claim 4, wherein the retroviral gag and pol proteins are from an ecotropic retrovirus.

6. The cultured packaging cell of claim 1, wherein the vertebrate cell is an avian or mammalian cell.

7. The cultured packaging cell of claim 1, wherein said first and second vectors are integrated in a chromosome of the packaging cell.

8. A cultured packaging cell for producing a replication-defective retroviral vector particle, wherein the packaging cell is a vertebrate cell comprising:
   a first vector encoding a retroviral env protein comprising amino acid residues of a 10A1 retrovirus that direct binding of the retroviral vector particle to Glvr-1 or Ram-1 retroviral receptors on a target cell;
   a second vector encoding retroviral gag and pol proteins; and
   a third vector comprising a sequence encoding a heterologous protein of interest, wherein said env, gag, and pol proteins are expressed in said packaging cell, and wherein a replication-defective retroviral vector particle is produced by assembly of said env, gag, and pol proteins such that said vector particle binds to Glvr-1 and Ram-1 retroviral receptors of target cells.

9. A method for producing a replication-defective retroviral vector particle encoding a heterologous protein of interest comprising:
   transducing or transfecting the retroviral packaging cell of claim 1 with (a) a replication defective virus particle which comprises virus RNA transcribed from a recombinant DNA provirus, said provirus comprising virus long terminal repeat sequences (LTRs), a retrovirus packaging sequence, and a heterologous gene, or (b) a vector comprising said provirus,
   expressing in said packaging cell the retroviral env gag and pol proteins, and the heterologous protein of interest; and
   producing a replication-defective retroviral vector particle that binds to Glvr-1 and Ram-1 retroviral receptors of target cells.

10. The method of claim 9, wherein the replication-defective retroviral vector particle encoding the heterologous protein of interest is produced at a titer of at least $10^5$ FFU/ml medium.

11. The method of claim 10, wherein the replication-defective retroviral vector particle encoding the heterologous protein of interest is produced at a titer of at least $10^7$ FFU/ml medium.

12. The replication-defective retroviral vector particle containing a sequence encoding the heterologous protein of interest produced by the method of claim 9 wherein said replication-defective retroviral vector particle comprises a retroviral env protein comprising amino acid residues of a 10A1 retrovirus such that said retroviral vector particle binds to Glvr-1 and Ram-1 retroviral receptors of target cells."

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1234 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| GCATGCCGCA | GGTATTGGGA | ACTGACAATG | GGCCTGCCTT | CGTCTCCAAG | GTGAGTCAGA | 60 |
| CAGTGGCCGA | TCTGTTGGGG | ATTGATTGGA | AATTACATTG | TGCATACAGA | CCCCAAAGCT | 120 |
| CAGGTCAGGT | AGAAAGAATG | AATAGGACCA | TCAAGGAGAC | TTTAACTAAA | TTAACGCTTG | 180 |
| CAACTGGCTC | TAGAGACTGG | GTGCTCCTAC | TCCCCTTAGC | CCTGTACCGA | GCCCGCAACA | 240 |
| CGCCGGGCCC | CCATGGCCTC | ACCCCATATG | AGATCTTATA | TGGGGCACCC | CCGCCCCTTG | 300 |
| TAAACTTCCC | TGACCCTGAC | ATGACCAGAG | TTACTAACAG | CCCCTCTCTC | CAAGCTCACT | 360 |
| TACAGGCTCT | CTACTTAGTC | CAGCACGAAG | TTTGGAGACC | ACTGGCGGCA | GCTTACCAAG | 420 |
| AACAACTGGA | CCGGCCGGTG | GTGCCTCACC | CTTACCGGGT | CGGCGACACA | GTGTGGGTCC | 480 |
| GCCGACATCA | AACCAAGAAC | CTAGAACCTC | GCTGGAAAGG | ACCTTACACA | GTCCTGCTGA | 540 |
| CCACCCCCAC | CGCCCTCAAA | GTAGACGGTA | TCGCAGCTTG | GATACACGCA | GCCCACGTAA | 600 |
| AGGCGGCCGA | CACCGAGAGT | GGACCATCCT | CTGGACGGAC | ATGGCGCGTT | CAACGCTCTC | 660 |
| AAAACCCCCT | CAAGATAAGA | TTAACCCGTG | GAAGCCCTTA | ATAGTCATGG | GAGTCCTGTT | 720 |
| AGGAGTAGGG | ATGGCAGAGA | GCCCCCATCA | GGTCTTTAAT | GTAACCTGGA | GAGTCACCAA | 780 |
| CCTGATGACT | GGGCGTACCG | CCAATGCCAC | CTCCCTCCTG | GGAACTGTAC | AAGATGCCTT | 840 |
| CCCAAAATTA | TATTTTGATC | TATGTGATCT | GGTCGGAGAG | GAGTGGGACC | CTTCAGACCA | 900 |
| GGAACCGTAT | GTCGGGTATG | GCTGCAAGTA | CCCCGCAGGG | AGACAGCGGA | CCCGGACTTT | 960 |
| TGACTTTTAC | GTGTGCCCTG | GGCATACCGT | AAAGTCGGGG | TGTGGGGGAC | CAGGAGAGGG | 1020 |
| CTACTGTGGT | AAATGGGGGT | GTGAAACCAC | CGGACAGGCT | TACTGGAAGC | CCACATCATC | 1080 |
| GTGGGACCTA | ATCTCCCTTA | AGCGCGGTAA | CACCCCCTGG | GACACGGGAT | GCTCTAAAGT | 1140 |
| TGCCTGTGGC | CCCTGCTACG | ACCTCTCCAA | AGTATCCAAT | TCCTTCCAAG | GGGCTACTCG | 1200 |
| AGGGGGCAGA | TGCAACCCTC | TAGTCCTAGA | ATTC | | | 1234 |

( 2 ) INFORMATION FOR SEQ ID NO:2:

( i ) SEQUENCE CHARACTERISTICS:
        ( A ) LENGTH: 1237 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| GCATGCCTCA | GGTGTTGGGA | ACTGACAATG | GGCCTGCCTT | CGTCTCCAAG | GTGAGTCAGA | 60
| CAGTGGCCGA | TCTGCTGGGG | ATTGATTGGA | AATTACATTG | TGCGTACCGA | CCCCAAAGCT | 120
| CAGGTCAGGT | AGAAAGAATG | AATAGGACCA | TCAAGGAGAC | TTTAACTAAA | TTAACGCTTG | 180
| CAACTGGCAC | TAGAGACTGG | GTACTCCTAC | TTCCCTTAGC | CCTCTACCGA | GCCCGCAACA | 240
| CTCCGGGCCC | CCATGGACTC | ACTCCGTATG | AAATCCTGTA | TGGGGCGCCC | CCGCCCCTTG | 300
| TTAATTTCCA | TGATCCTGAA | ATGTCAAAGT | TTACTAATAG | CCCCTCTCTC | CAAGCTCACT | 360
| TACAGGCCCT | CCAAGCAGTA | CAACGAGAGG | TCTGGAAGCC | ACTGGCCGCT | GCCTATCAGG | 420
| ACCAGCTGGA | CCAGCCAGTG | ATACCACACC | CCTTCCGTGT | CGGCGACACC | GTGTGGGTAC | 480
| GCCGGCACCA | GACTAAGAAC | TTGGAACCTC | GCTGGAAAGG | ACCCTACACC | GTCCTGCTGA | 540
| CCACCCCCAC | CGCTCTCAAA | GTAGACGGCA | TCGCTGCGTG | GATCCACGCC | GCTCACGTAA | 600
| AGGCGGCGAC | AACCCCTCCG | GCCGGAACAG | CATCAGGACC | GACATGGAAG | GTCCAGCGTT | 660
| CTCAAAACCC | CTTAAAGATA | AGATTAACCC | GTGGAAGTCC | TTAATGGTCA | TGGGGGTCCT | 720
| ATTAAGAGTA | GGGATGGCAG | AGAGCCCCCA | TCAGGTCTTT | AATGTAACCT | GGAGAGTCAC | 780
| CAACCTGATG | ACTGGGCGTA | CCGCCAATGC | CACCTCCCTT | TTAGGAACTG | TACAAGATGC | 840
| CTTCCCAAGA | TTATATTTTG | ATCTATGTGA | CCTGGTCGGA | GAAGAGTGGG | ACCCTTCAGA | 900
| CCAGGAACCA | TATGTCGGGT | ATGGCTGCAA | ATACCCCGGA | GGGAGAAAGC | GGACCCGGAC | 960
| TTTTGACTTT | TACGTGTGCC | CTGGGCATAC | CGTAAAATCG | GGGTGTGGGG | GGCCAAGAGA | 1020
| AGGCTACTGT | GGTGAATGGG | GTTGTGAAAC | CACCGGACAG | GCTTACTGGA | AGCCCACATC | 1080
| ATCTGGGACC | TAATCTCCCT | TAAGCGCGGT | AACACCCCCC | TGGGACACGG | GATGCTCCAA | 1140
| AATGGCTTGT | GGCCCCTGCT | ATGACCTCTC | CAAGGTATCC | AATTCCTTCC | AAGGGGCTAC | 1200
| TCGAGGGGGC | AGATGCAACC | CTCTAGTCCT | AGAATTC | | | 1237

( 2 ) INFORMATION FOR SEQ ID NO:3:

( i ) SEQUENCE CHARACTERISTICS:
        ( A ) LENGTH: 735 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| GCATGCCTCA | GGTATTGGGA | ACTGACAATG | GGCCTGCCTT | CGTCTCCAAG | GTGAGTCAGA | 60
| CAGTGGCCGA | TCTGTTGGGG | ATTGATTGGA | AATTACATTG | TGCATACAGA | CCCCAAAGCT | 120
| CAGGCCAGGT | AGAAAGAATG | AATAGAACCA | TCAAGGAGAC | TTTAACTAAA | TTAACGCTTG | 180
| CAACTGGCTC | TAGAGACTGG | GTGCTCCTAC | TCCCCTTAGC | CCTGTACCGA | GCCCGCAACA | 240
| CGCCGGGCCC | CCATGGCCTC | ACCCCATATG | AGATCTTATA | TGGGGCACCC | CCGCCCCTTG | 300
| TAAACTTCCC | TGACCCTGAC | ATGACAAGAG | TTACTAACAG | CCCCTCTCTC | CAAGCTCACT | 360
| TACAGGCTCT | CTACTTAGTC | CAGCACGAAG | TCTGGAGACC | TCTGGCGGCA | GCCTACCAAG | 420
| AACAACTGGA | CCGACCGGTG | GTACCTCACC | CTTACCGAGT | CGGCGACACA | GTGTGGGTCC | 480
| GCCGACACCA | GACTAAGAAC | CTAGAACCTC | GCTGGAAAGG | ACCTTACACA | GTCCTGCTGA | 540

-continued

| | | | | | | |
|---|---|---|---|---|---|---|
| CCACCCCCAC | CGCCCTCAAA | GTAGACGGCA | TCGCAGCTTG | GATACACGCC | GCCCACGTGA | 600 |
| AGGCTGCCGA | CCCCGGGGGT | GGACCATCCT | CTAGACTGAC | ATGGCGCGTT | CAACGCTCTC | 660 |
| AAAACCCCTT | AAAAATAAGG | TTAACCCGCG | AGGCCCCCTA | ATCCCCTTAA | TTCTTGATGC | 720 |
| TCAGAGGGGT | CAGTA | | | | | 735 |